Figure 3:
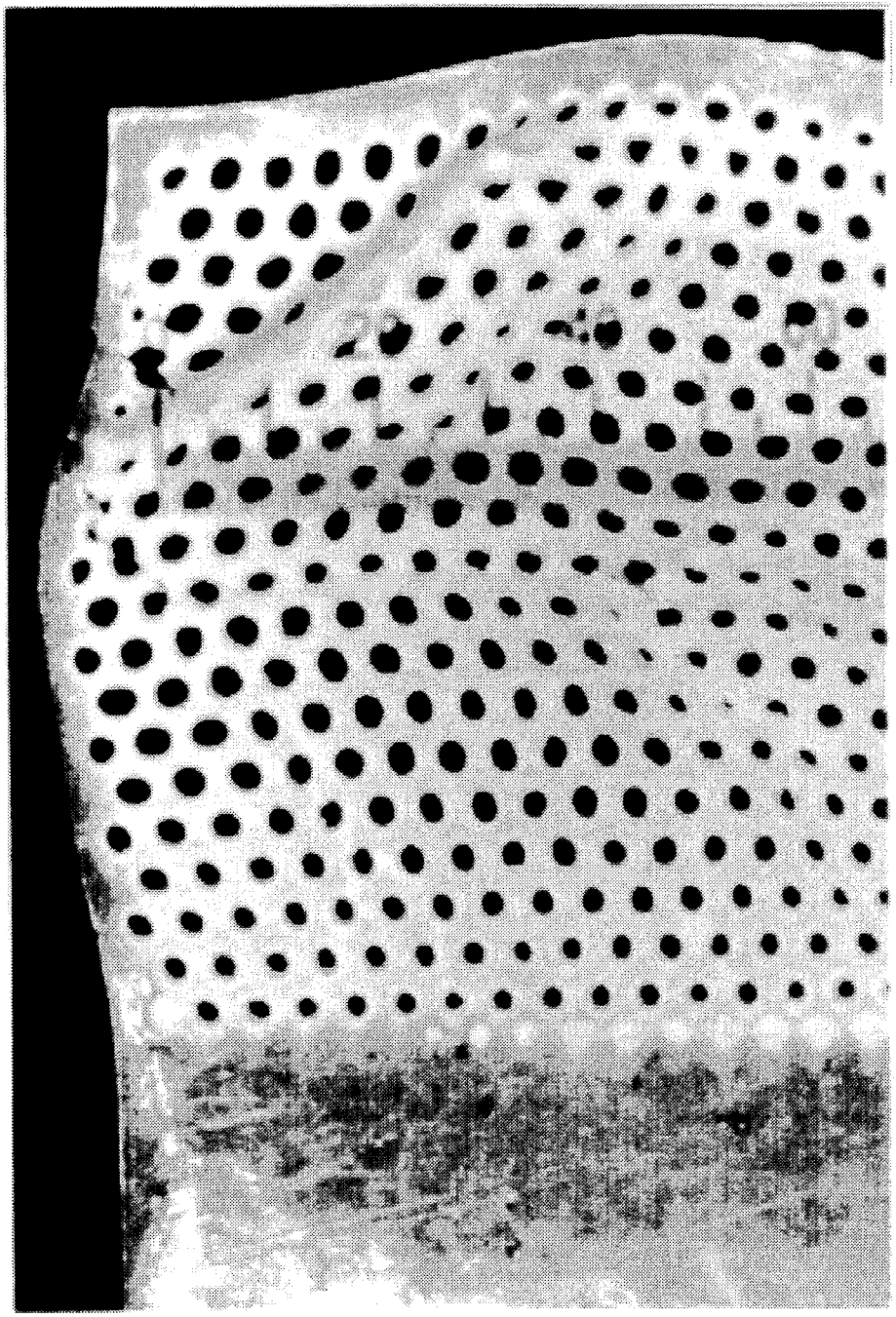

United States Patent [19]

Mathiesen et al.

[11] Patent Number: 5,486,546
[45] Date of Patent: Jan. 23, 1996

[54] METHOD OF PRODUCING A MICROSTRUCTURE IN A BIORESORBABLE ELEMENT

[76] Inventors: Torbjorn Mathiesen, Bandhagsplan 9, S-13224 Bandhagen; Gunnar Bernhard, Mastvagen 12, 181 43 Lidingo, both of Sweden; Phil Rumsby, Longhamborough, England

[21] Appl. No.: 162,053

[22] PCT Filed: Jun. 10, 1992

[86] PCT No.: PCT/SE92/00404

§ 371 Date: Feb. 7, 1994

§ 102(e) Date: Feb. 7, 1994

[87] PCT Pub. No.: WO92/22336

PCT Pub. Date: Dec. 23, 1992

[30] Foreign Application Priority Data

Jun. 10, 1991 [SE] Sweden ................................... 9101752

[51] Int. Cl.$^6$ ..................................................... C08G 63/02
[52] U.S. Cl. ................................ 522/165; 522/2; 264/482
[58] Field of Search ............................... 264/25; 522/162, 522/2

[56] References Cited

U.S. PATENT DOCUMENTS

| | | | |
|---|---|---|---|
| 4,417,948 | 11/1983 | Mayne-Banton et al. | 156/643 |
| 4,824,699 | 4/1990 | Woo et al. | 427/307 |
| 5,017,423 | 5/1991 | Bossmann et al. | 428/224 |
| 5,207,955 | 5/1993 | Esrom et al. | 264/22 |

FOREIGN PATENT DOCUMENTS

| | | |
|---|---|---|
| 0176895 | 4/1986 | European Pat. Off. . |
| 2053789 | 2/1981 | United Kingdom . |
| WOA1-87/03021 | 5/1987 | WIPO . |
| WOA1-90/07308 | 7/1990 | WIPO . |

*Primary Examiner*—W. Robinson Clark
*Attorney, Agent, or Firm*—Kenyon & Kenyon

[57] ABSTRACT

Method of producing a microstructure in a bioresorbable element comprising a material consisting of a major portion of at least one polymer selected from the group including aliphatic polyesters and aliphatic polycarbonates and copolymers thereof. The microstructure is accomplished by using an excimer laser which is operated at a maximum wavelength of 248 nm.

7 Claims, 6 Drawing Sheets

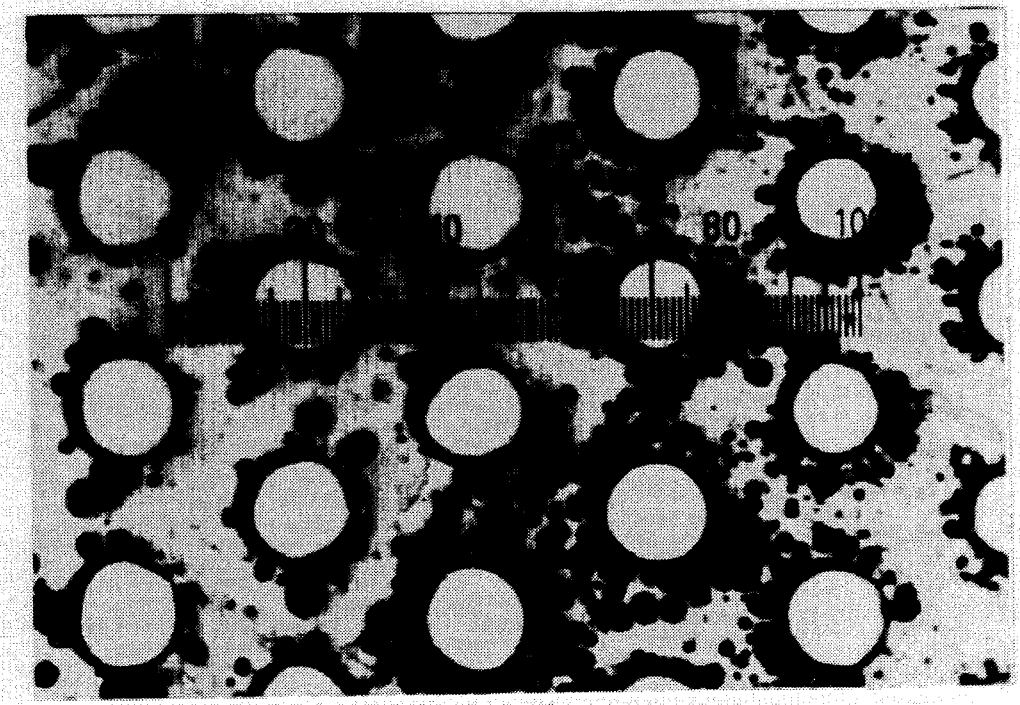
F I G. 1
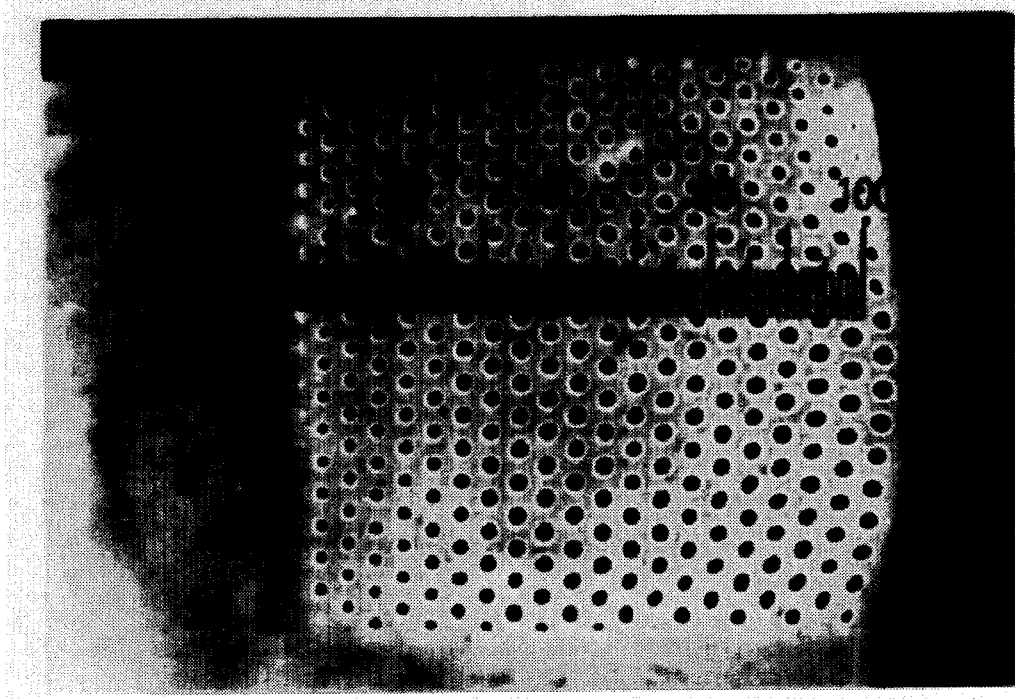
F I G. 2

METHOD OF PRODUCING A MICROSTRUCTURE IN A BIORESORBABLE ELEMENT

The present invention relates to a method of producing microstructures in a bioresorbable element to be used for medical applications in a living organism. The element could be used e.g. to selectively influence the healing process by separating and guiding the tissues surrounding the element in such a way that regeneration is achieved, as described in WO 90/07308. Typically, the bioresorbable materials used for the elements are made from homopolymers or copolymers that have been formed by polymerization of monomers such as hydroxy acids, hydroxy ether acids, lactones and cyclic dimers thereof, or cyclic carbonates. Examples of such monomers are glycolic acid, lactic acid, ε-caprolactone, trimetylene carbonate, paradioxanone, 1,5-dioxepan-2-one, valerolactone and β-butyrolactone. The element may also be made from the naturally occurring polymer known as hydroxy butyrate or any copolymer of hydroxy butyrate and hydroxy valerate. The use of such materials in said element is preferred because these materials degrade in contact with water and thereby disintegrate into smaller molecules that are metabolized or excreted from the body. The tissue an then heal without disturbances, and no foreign material is left in the body after complete healing, which eliminates the long term risks for e.g. infections and other complications.

An element that is to be used in the process of regeneration of living tissues, also should have certain properties which are not related to the material. Such properties may include:
1) the element should be anchored at the implant site;
2) the element should partly or totally separate different kinds of tissue and thereby allow for an early integration or a pre-programmed initial period of total separation before integration of two different tissues;
3) the element should block tissue growth into or through the element for a longer period of time.

Said properties can be achieved by incorporation of a microstructure into the element or the surface thereof. Typically, this microstructure could have dimensions as large as several square millimeters and as small as a few square micron and could cover the surface from 0 to 80%, preferably in the range of 2 to 50%. The microstructure may form a continuous pattern or a discontinuous pattern including microstructure areas positioned close to each other or further away from each other. The microstructure could take different shapes such as apertures e.g. in the form of circles or rectangles, grooves, and indentations, e.g. blind holes.

Prior art technique that can be used for the purpose of obtaining related or comparable microstructures includes mechanical punching, freeze drying, extraction or sublimation of pre-placed crystals, and infrared laser technology.

Mechanical punching is difficult to perform if the transverse dimension of the aperture to be punched is smaller than 70 μm, and will be difficult also in case of larger dimension is many apertures are to be made within a small area. The success of mechanical punching is depending extensively on the mechanical properties of the material in which the apertures shall be made, and the three-dimensional design of the element. An obvious limitation of this technique is the fact that only through apertures can be made in the element.

By the freeze drying technique only random patterns of pores or textures can be produced within or on the surface of the element. The same is true also for the extraction and sublimation technique where it is difficult to position crystals in a structured, planned fashion. The sublimation method may result in difficulties during the sublimation procedure to remove all of the preplaced crystals, and the extraction method may result in retention of water or organic solvent in the element after the extraction procedure that could be delicate to remove. Moreover, it is difficult to remove the crystals completely by extraction or sublimation without at the same time damaging or destroying the element.

Infrared laser technology has been used for many years in the form of $CO_2$ and Nd:YAG lasers. Typical use of these lasers, operating at a wave-length of 10.6 and 1.06 μm, respectively, is for cutting or drilling purposes, the materials hit by the beam being melted and combusted or vaporized. The beam, the wave-length of which is in the infrared portion of the electromagnetic spectrum, creates an intense heat in the material due to lattice vibration. This principle of creating microstructures cannot be used in combination with thermally sensitive polymers such as poly-lactides or poly-glycolides, because either the microstructure made will be destroyed by the intense heat, or the material in the neighbourhood of the microstructures made will be heavily degraded, which will impart to the element low dimensional stability after implantation, due to large water uptake followed by swelling. All the above mentioned techniques have such limitations or disadvantages that they cannot be used for the purpose of producing micro-structures of desired shape and dimensions.

During the 80s, excimer laser technology has been developed. These lasers operate with a pulsed beam having a distinct wave-length in the UV-light range such as, but not limited to, 308, 248 and 193 nm. The high photon energy of such light is of the same order as that required for breaking up chemical bonds in most organic molecules. If the molecules of the material, wherein the microstructures shall be made, have such a chemical structure for which the absorption coefficient of the specific wave-length used is high, most of the output energy of these lasers, that reaches the material, will be consumed by the photo chemical bond-breaking process that will take place in the material, and a very small portion of the energy will be converted into thermal energy which can heat up the material. As a consequence of such heating portions or areas of the element being processed which should be left unaffected, may be degraded or melted. It is therefore very important to keep the proportion of energy, that is converted into thermal energy at a low level. This is especially true for such thermal sensitive materials as the group of aliphatic polyesters or polycarbonates mentioned above. The initiation of the photo ablation process, e.g. removal of material from the surface by means of light, is also dependent of the energy density of the laser beam at the surface of the material. A certain barrier called the threshold energy, must be overcome in order to start the ablation process. The threshold energy is the energy density per pulse required to break a sufficient number of bonds in the surface layer of the material so that the pressure due to the large number of small molecules formed builds up to a sufficiently high level for the degraded material to be expelled. The technique has been used for some years on polymers containing aromatic groups in their repeating unit such as aromatic polyesters e.g. poly-ethyleneterephtalate, aromatic polycarbonates and poly-imides, these types of materials having a high absorption coefficient at the typical excimer laser wave length and also known as polymers having a high thermal stability. Such polymers are mentioned in WO 87/03021 which describes a method using, among others, excimer lasers for producing microstructures in shape of elevations and depressions in fibres and similar elements. The typical depth or height in that case ranges from 0.1 to 2 μm but also 10 μm is mentioned. The spacing between the elevations or depressions ranges from 1 to 5 μm. The laser energy density ranges from 5 to 500 mJ/cm² and preferably between 20–50 mJ/cm². The increased specific surface area of the fibres, accomplished by the microstructure, yields structures with excellent filtration properties and also great dye absorption capacity. Said structures are also claimed to provide advantages in the field of medicine, surgical sewing materials, prosthetic articles and artificial veins being mentioned.

Bioresorbable elements, that is elements made of polymers which are hydrolysed in contact with water in the living body, the hydrolysis products being absorbed by the surrounding tissue and metabolized or excreted, which are used for implantation are commonly made of a material consisting of a major portion (usually at least 70% by weight) of at least one polymer selected from the group including aliphatic polyesters and aliphatic polycarbonates or copolymers thereof. Examples of such polymers are poly-lactide, poly-glycolide, poly-ε-caprolactone, poly-valerolactone, poly-hydroxybutyrate, poly-1,4-dioxan-2-one, poly-1,5-dioxepan-2-one, polytrimethylene carbonate or any copolymers or blends thereof. These materials, being aliphatic polyesters, possess a very weak UV-light absorbing ester bond in the UV region above 200 nm. They are also known to be very unstable when exposed to heat. This is even more so if the material is plasticized in order to obtain a softer material. Usually the plasticizer chosen for the above mentioned polymers is ethyl, butyl and hexyl esters of acetylated or non-acetylated citric acid ester, triacetin or an oligomer, 1 to 10 repeating units, made from one of the monomers mentioned above although the choice is not limited to these materials.

The present invention provides a method of producing a microstructure in a bioresorbable element comprising a material consisting of a major portion of at least one polymer selected from the group including aliphatic polyesters or aliphatic polycarbonates or copolymers thereof, by the use of an excimer laser operated at a maximum wave-length of 248 nm and an energy density at the surface of the material of at least 200 mJ/cm².

By this method minimal degradation in the element is achieved, which reduces the problem of high water absorption. High water absorption leads to swelling which causes deformation of the element and is especially pronounced in copolymers of glycolide and lactide but also in pure poly-lactide. Incorporation of a microsucture into a medical device always have one or more specific purposes, some of these having been mentioned above. It is important to maintain the shape of these structures over a certain period of time. It is commonly known that resorbable polymers starts to deform when the molecular weight have been reduced by hydrolysis to such a point that the mechanical strength of the polymeric material is lower than the force or pressure acting on the material from the inside by the hydrolysis products and the absorbed water. The first step in this process of resorption is the water uptake which cause stress release and volume changes, swelling, in the element which therefore starts to deform and at a later stage breaks up into fragments due to the on-going hydrolysis. This problem of dimensional stability of a preshaped element used for implantation is more pronounced in elements made of polymeric materials containing polymers with low molecular weights, and therefore it is of special interest to minimize thermal or any kind of degradation in the element while exposing the element to the laser beam for incorporation of the microstucture. If too much degradation occurs in areas which should not be processed by the laser beam, the dimensional stability of the element will be greatly reduced.

The microstructures created must, in order to function successfully in guiding the tissue growth, have dimensional stability over a certain period of time after implantation. In many applications the element should be made of a soft malleable material rather than the stiff homo- or copolymers of poly-glycolide and poly-lactide. Poly-glycolide, poly-lactide and copolymers or blends thereof can be plasticized to possess softness and malleability. However, a drawback of using plasticizers is swelling of the material due to water uptake. The degree of water uptake can be controlled by the choice of plasticizer and polymer used. In all cases the swelling also depend on the molecular weight of the polymer used as the main matrix component. It is thus very important that the laser treatment in order to create the microstructures does not cause (extensive chain scission at other places than just where the microstructure is to be created, i.e. the thermal degradation of the material due to heat build-up must be kept at a minimum.

With reference to the accompanying drawings in which

Figure 4:
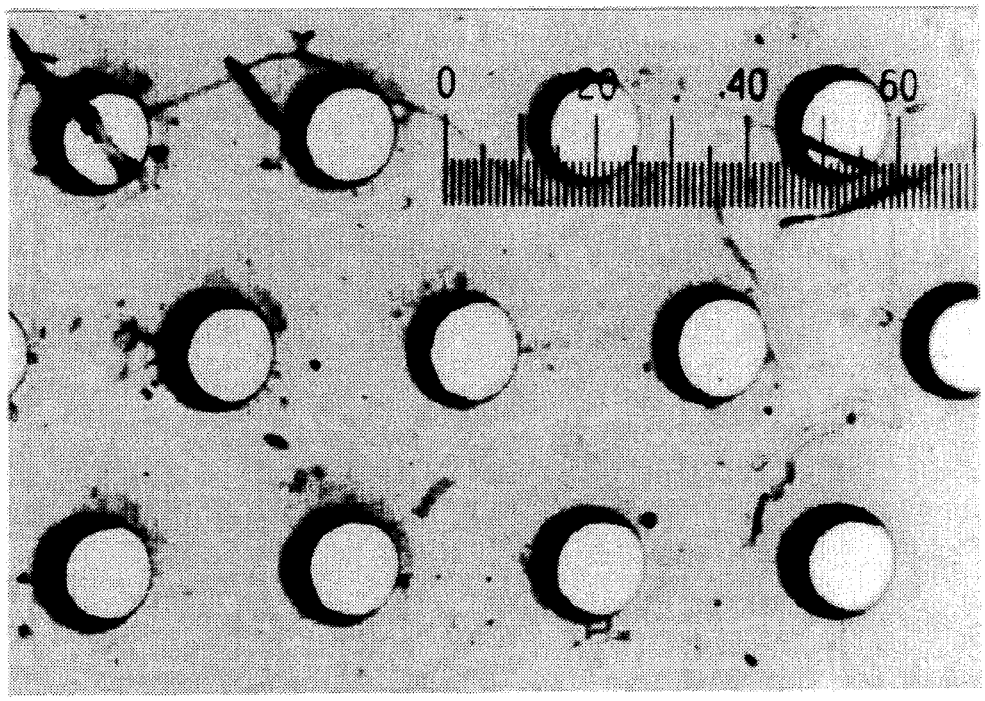
Figure 5:
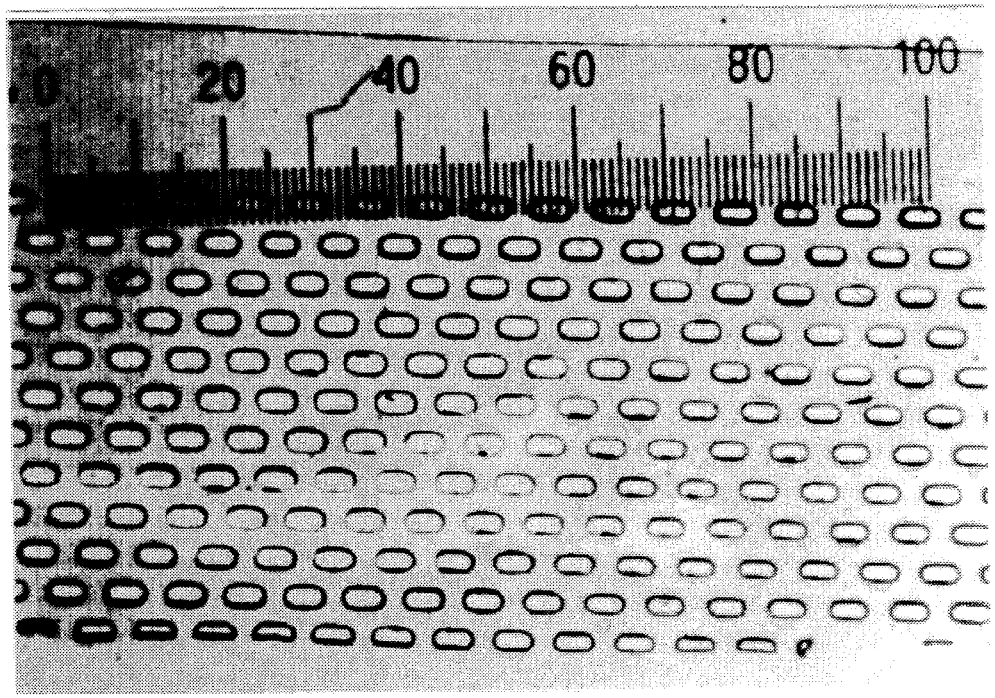
Figure 6:
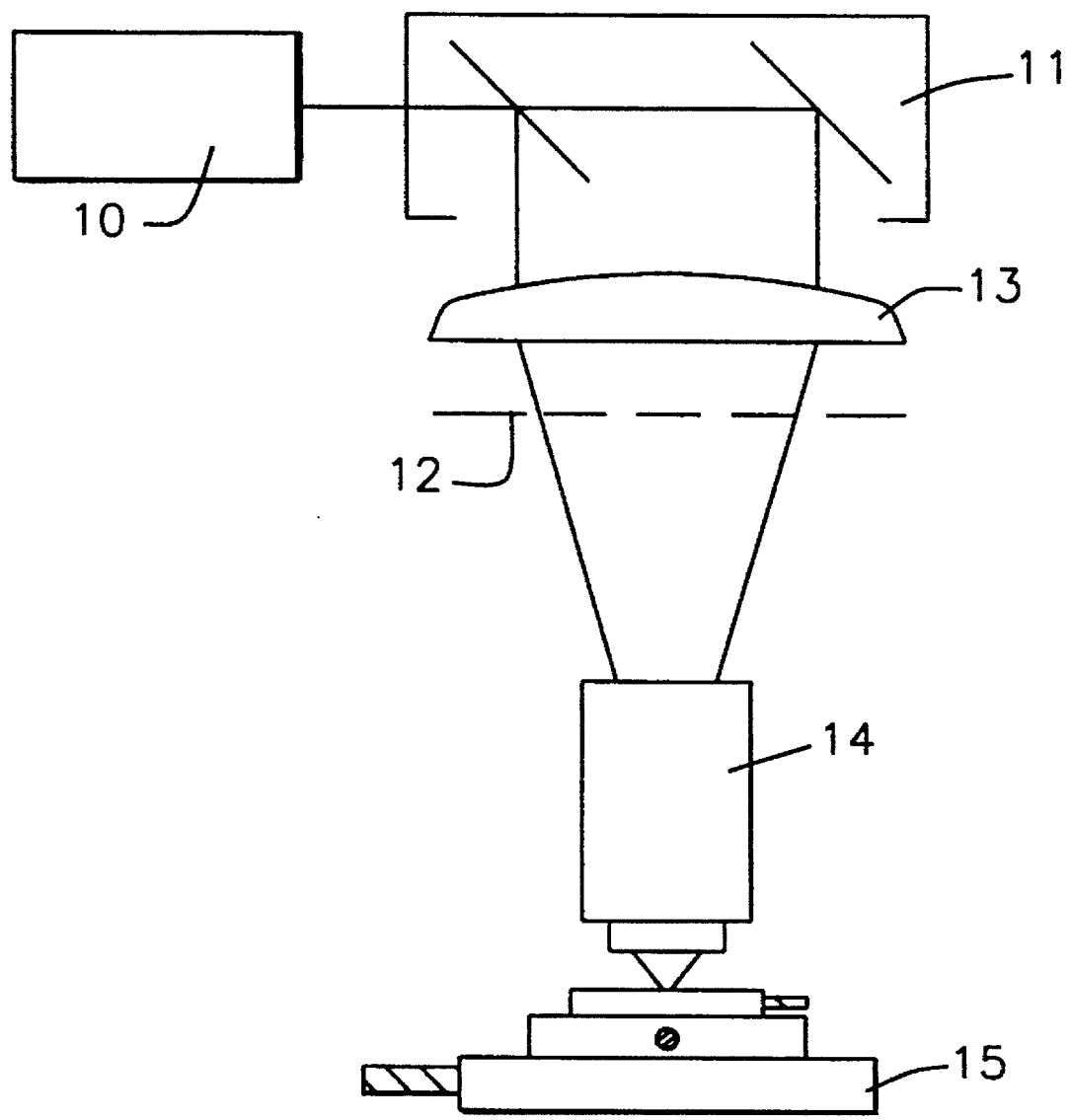
Figure 7:
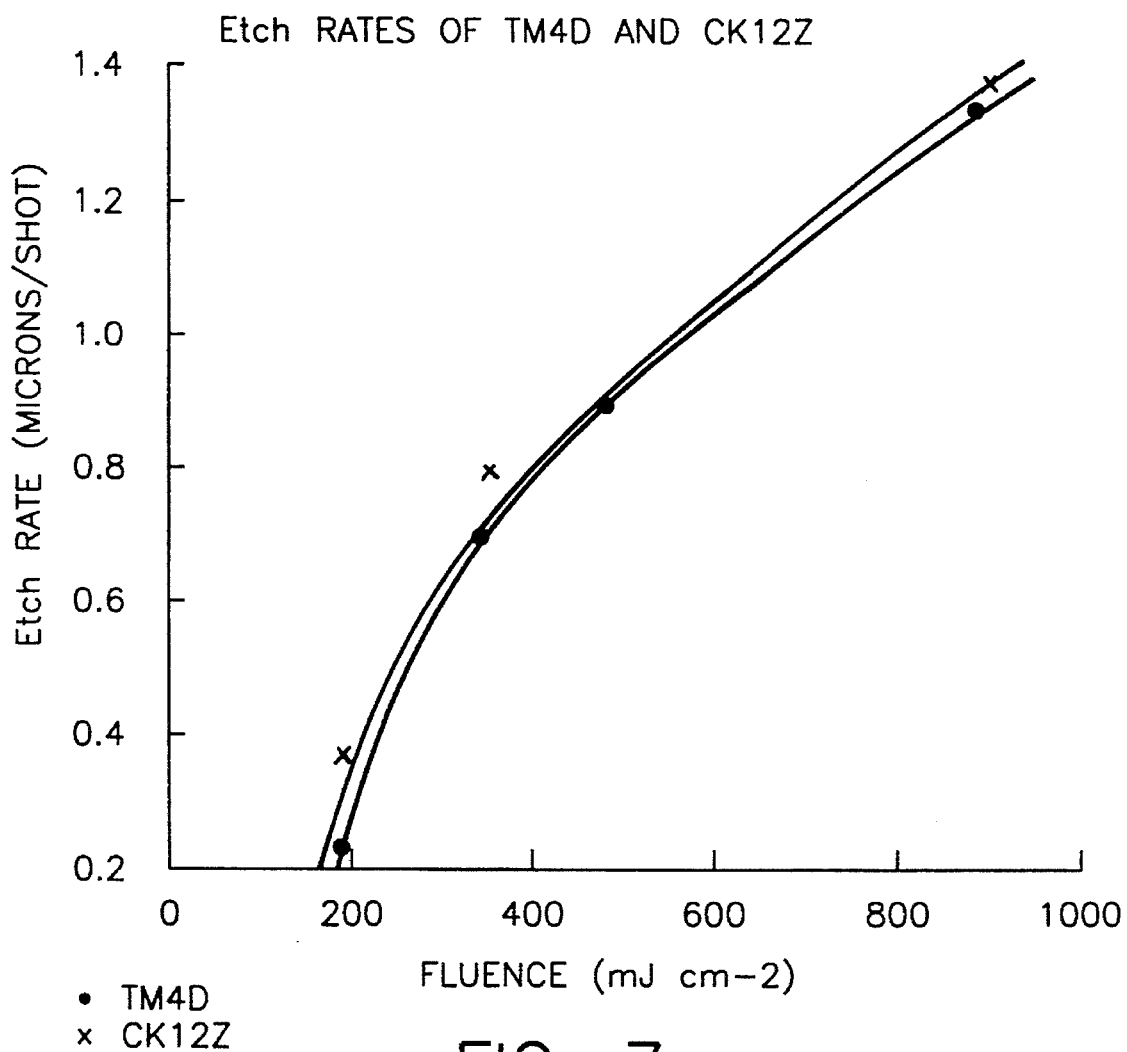
Figure 8:
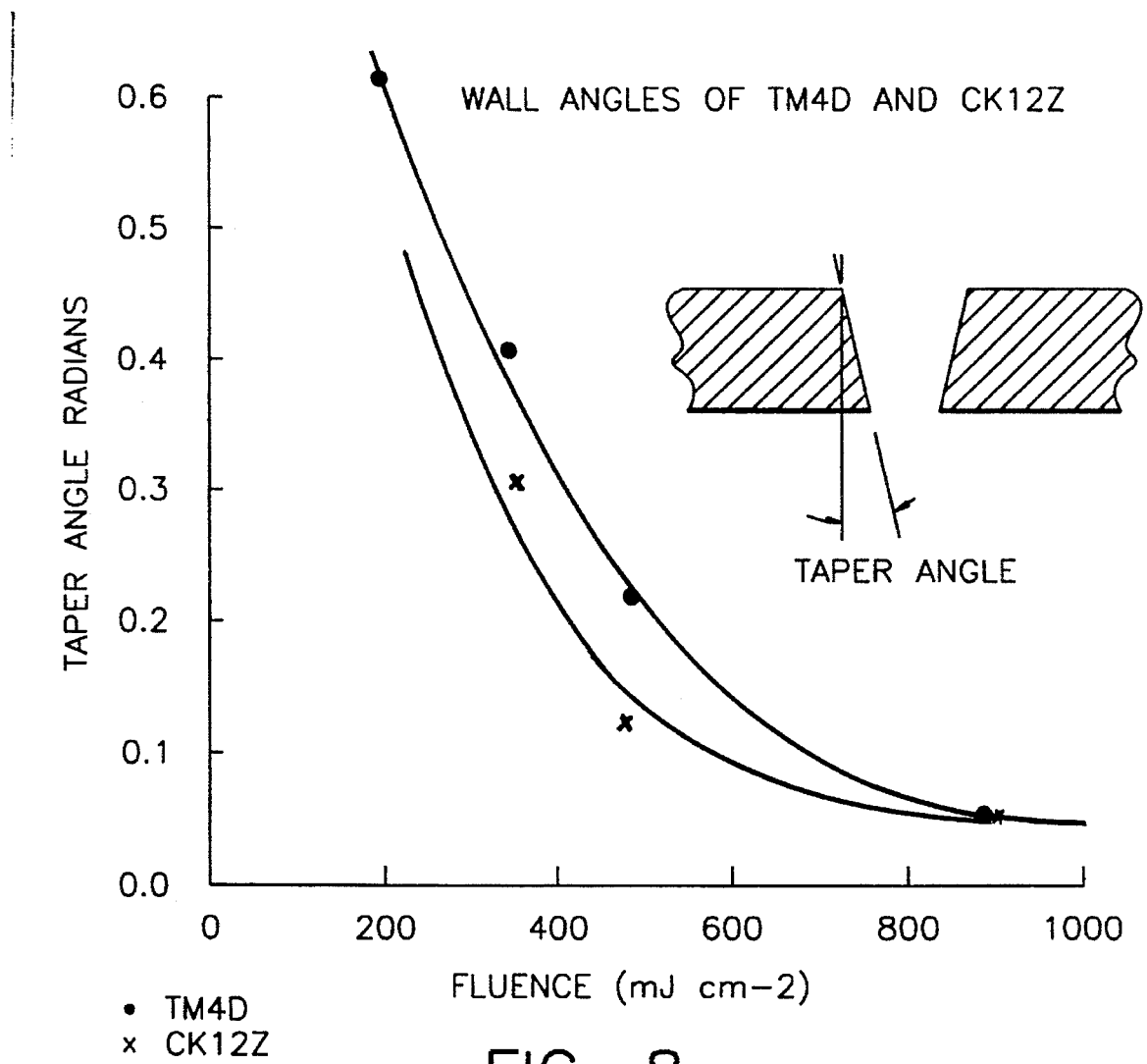

FIG. 1 is a micrograph of an element having a microstructure which has been produced by an excimer laser operating at 248 nm, FIG. 2 is a micrograph of an element having a microstructure which has been produced by an excimer laser operating at 248 nm and which has been immersed in a saline solution for 24 hours, FIG. 3 is a micrograph of an element of the type shown i FIG 2, which has been immersed in a saline solution for 15 days, FIG. 4 is a micrograph of an element having a microstructure which has been produced by an excimer laser operating at 193 nm, FIG. 5 is a micrograph of an element have an alternatively shaped microstructure which has been produced by an excimer laser operating at 193 nm and FIG. 6 is a schematic view of a laser and optical set-up for the production of said microstructures, FIG. 7 is a graph showing the etch rate or ablated depth in micron/laser pulse vs. energy density or fluency in mJ/cm, and FIG. 8 is a graph showing the taper angle in radians vs. energy density or fluency in mJ/cm², including also a diagrammatic figure that defines the taper angel, examples will be described, which have been performed and wherein holes with a typical diameter of 200 μm and a centre distance between the holes of typically 400 μm have been made. The holes were arranged in a hexagonal pattern over the surface of a 100 μm thick film of plasticized poly-lactic acid. Two compositions were used:

1) 75% by weight poly-d,1-lactic acid and 10% by weight poly-1-lactic acid plasticized with 15% by weight acetyl-tri-n-butyl citrate, and 2) 80% by weight poly-d,1-lactic acid plasticized with 20% by weight ethyl terminated oligomer of lactic acid.

The wave-lengths used in these experiments were 308, 248 and 193 nm, and the pulse rate was kept low, typically less than 5 Hz. At 308 nm the ablation process did not start, no holes were created in the surface.

Photo ablation occurred in both of the two different types of film described above when the wave-length of the laser light was 248 or 193 nm. It was, however, a marked difference in the result when the two different wave-lengths were used; 248 nm produced holes of good quality at low pulse rate. However, as can be seen in FIG. 1, an increase of the pulse rate created holes which had pronounced rounded edges because the material had melted. Also small bubbles could be found, which are believed to be gas pockets, around the holes. These gas pockets, most pronounced for material composition 2, are certainly due to thermal degradation of the polymer but may also be due to a residue of water, usually found in these kinds of material, that vaporises at heating of the material. The vapour or gas formed due to thermal degradation, will expand in the material to form bubbles.

In order to achieve good results as judged by visual inspection of the holes made, the polymer film had to rest against a backing material, e.g. steel, glass or any inert material, that can take up and transfer the heat built up in the polymer film. To test the "in vitro" dimensional stability of the films containing the microstructures structures that were made at low pulse rate and the proper choice of backing, the films were placed in a phosphate buffered saline solution of pH 7.4 and incubated at 37° C. A result of such a test is shown in FIG. 2. After 1 day an opaque ring could easily be seen around each hole. This opaque colour seen in the material close to and at the wall zone of the holes is typically formed in aliphatic polyesters due to water uptake and indicates a rather fast and large water uptake in the area that has been affected by the laser beam. The explanation for this goes back to the thermal breakdown that occurs due to heat build-up in the material not hit by the laser beam, which will create a large number of free chain ends in the poly-lactic acid polymer. The chain ends, being of polar nature bring about a more hydrophilic environment in the polymer and, thus, a faster water absorption may occur.

FIG. 3 shows that in time, typically 5–15 days, this will lead to deformation of the microstructures s the material starts to swell, and ultimately ruin said structures. Even though it is possible to make microstructures that look good by visual inspection, by using a 248 nm excimer laser, these structures will start to deform soon after implantation of the element due to the chemical alteration of the polymer composition taking place under the influence of the thermal effects.

FIG. 4 and FIG. 5 show the result when the laser was operated at 193 nm, FIG. 5 showing rectangular holes. The results turned out to be quite different, and no thermal damage could be detected around the holes, even at pulse rates up to 50 Hz. It was not necessary to use any form of backing material, and incubation "in vitro" showed that the water uptake was very much the same as for untreated films. This shows that degradation due to heat built up and also UV-light scattering is very low at 193 nm and that most of the energy is used for the ablation process. The holes are very exact, and no more swelling of the microstructure could be observed after 20 days than that to be expected normally in polymers of these types.

FIG. 6 shows schematically the laser and optical set-up which could be used to create a certain pattern or microstructure on the surface of an element. The beam from a laser 10, scans by means of a mirror unit 11 over the surface of a mask 12 made of metal, which is used to mask off the laser beam. The image of the mask is projected on the surface of the element to be processed by a field lens 13 and an imaging lens 14. By the use of an x-y table 15 the element can be moved in such a way that it will be possible to scan large objects and at the same time to maintain the energy density required for the desired photo ablation process to take place.

It is furthermore of great importance when processing sensitive materials as mentioned above to maintain focus of the projected mask over the area of the element to be processed. To maintain focus it is necessary to keep constant the distance between the mask and the lens and the distance between the lens and the element to be processed. This can be done either by holding the element rigidly in a frame or to support it on some structure so that the distance between the lens and the element is kept constant to a high degree of accuracy. Such a frame or support is preferably made from metal or an equivalent material.

Instead of using a projecting system as that described above the microstructures can be produced in the element by having the mask in close contact with the element the problem of focusing the beam thereby being eliminated. The mask can also be lifted from the surface, typically 0 to 5 mm, preferably 0 to 1 mm, in order to minimize the risk of contamination of the element by foreign particles coming from the mask when the same is hit by the laser beam. Such contamination can typically be metal dust if the mask is made of a metal.

The following example illustrate the application of using the excimer laser in order to create a microstructure having the properties mentioned, in pure and plasticized polylactides of the compositions mentioned above.

EXAMPLE 1

The beam from an excimer laser, Questek 2440, operating at 193 nm (argon fluoride gas fill) giving out approximately 200 mJ of energy per laser pulse in an area close to 20×10 mm was focused by means of a spherical lens having a focal length of 350 mm. The beam was allowed to expand to a point where the size became approximately 7×3.5 mm. At this point the energy density in the beam approximate to 800 mJ/cm$^2$. This reduced beam was allowed to fall on the surface of an appropriate mask made of beryllium copper or other metallic material, clamped in the proximity of the polymer supported in a backing material so that during the cutting operation the mask could not move with respect to the polymer material. The separation between the mask and the polymer was 100 to 200 μm. In order to process a large area of polymer the beam was scanned over the mask and the polymer by moving the latter two items forward and backwards in the beam in a direction parallel to the smaller dimension of the laser beam cross section. The cutting process was continued until the beam was observed to pass through the film over the entire area. Care was taken to keep the laser pulse rate at a sufficiently low level so that thermal damage to the material did not occur. For a poly-lactide film of 130 μm thickness a maximum pulse rate of 30 Hz was used.

In this invention, using the laser set up as described in Example 1, the influence of the laser energy density on the shape of the microstructure being produced has been investigated. The microstructure may be in the form of perforations, blind holes or grooves which cover the surface of the element in a continuous or discontinuous pattern, spaced 1 to 800 μm, preferably 10 to 400 μm. Such microstructures could specifically be apertures going through the element or part of the element. Apertures necessary for nutrition across the element in the shape of a film or foil should have a diameter in the range of 1 to 30 μm. For tissue ingrowth into the element for the purpose of anchoring or integrating the element the dimensions 30–1000 μm and specifically 50 to 500 μm have been found very useful. In order to create microstructures with dimensions of 1 to 20000 μm, preferably in the range of 5–1000 μm, in bioresorbable materials of the types referred to it is necessary to exceed the threshold energy for the photo ablation process to occur. The effect of different energy densities on the shape of the microstructures made will be discussed with reference to the graph in FIGS.

7 and 8 wherein the material codes appearing in the graphs stand for

CK12Z: 75% by weight poly-d, 1-lactic acid and 10% by weight poly-1-lactic acid plasticized with 15% by weight acetyltri-n-butyl citrate, and TM4D: 80% by weight poly-d, 1-lactic acid plasticized with 20% by weight ethyl terminated oligomer of lactic acid-.graph Typically, the threshold energy, i.e. the energy density per pulse, is around 200 mJ/cm$^2$ for pure or plasticized poly-lactides as can be seen in FIG. 7. There is also an upper limit, around 1200 mJ/cm$^2$, set by the fact that beyond this point thermal effects commence and also the efficiency of removal of material is decreasing. For the purpose of producing the said microstructures it is necessary to have an energy at the surface of the element to be processed between 200 to 1200 mJ/cm2, preferably between 400 to 1000 mJ/cm2. All structures created by means of the excimer laser will be tapered, i.e. the input end of an aperture always will have a greater area than the output end. The taper angle depends on the material composition and the energy density of the beam as seen in FIG. 8. The taper angle can be very high for low energy densities, as seen in FIG. 8, but will decrease as the energy density is increased. Depending on the shaped of the microstructures to be made and the purpose of the same adjustment to the proper level of energy density is necessary. For example if a circular hole or perforation 100 µm in diameter is to be made in an element 100 µm thick by using an energy density of 300 mJ/cm$^2$, the output diameter of the hole will be about 20 µm, while if an energy density of 800 mJ/cm$^2$ is used, the output diameter will be 90 µm. It is therefore necessary to choose an energy density which gives an acceptable etch rate in combination with the desiered dimension of the microstructure. Such energy densities can be found to be in he range between 300 to 500 mJ/cm2 for thinner elements wherein ablation depths of up to 50 µm is required, and in the range of 500 to 1000 mJ/cm2, preferably in the range of 700 to 900 mJ/cm2 for thicker material where ablation depths up to 250 µm is required. For poly-lactide the angle of taper is within acceptable range for structures that have a depth of typically 250 µm or less, using an energy density of 800 mJ/cm$^2$.

A further example will be given in which the microstructure in the shape of perforations which go all the way through the element is made by utilizing the technique of projecting the image of the mask on the surface of the element to be processed, such a system being shown in FIG. 6.

EXAMPLE 2

The beam from an excimer laser, Lumonics Excimer 600, giving out approximately 200 mJ of energy at 193 nm was adjusted in size using an appropriate optical system so that the energy density of 100 mJ/cm$^2$ was obtained at the surface of an appropriate mask. An optical projection system consisting of a field lens and an imaging lens was set up to produce a reduced image of the mask at the surface of the polymer. For the particular example of cutting poly-lactide films of 130 µm thickness a x3 linear reduction system was used. For this material the poly-lactide film was held in a silica windowed cassette so that the poly-lactide was always maintained in a sterile environment. To cover a large area at the polymer the laser beam was scanned using moving mirrors over the area of the mask in an appropriate raster or linear scan pattern. During this process the corresponding x3 reduced pattern size of the polymer was also scanned. The process was continued until the required structure was drilled completely through the polymer film. The laser pulse rate used depended on the area of the polymer film scanned and on the scanning rate in order to keep the power input below a level that would not cause thermal damage to the material, e.g. for an area of 20×10 mm to be scanned of the polymer, the laser pulse rate was held below 30 Hz.

We claim:

1. A method of producing a microstructure in at least a portion of a bioresorbable aliphatic polymer material adapted to be employed in a living body, which process comprises exposing said material to energy from an excimer laser operated at a maximum wave length of 248 mm, wherein a major portion of said material comprises at least one aliphatic polyester or aliphatic polycarbonate polymer, or blends thereof, made from one or more monomers selected from the class consisting essentially of glycolic acid, glycolide, lactic acid, lactide, ε-caprolactone, trimethylene carbonate, paradioxanone, 1,5-dioxepan-2-one, valerolactone and β-bµyrolactone, and mixtures thereof.

2. Method as in claim 1, characterised in that the excimer laser is operated to produce an energy density at the workpiece below 1200 mJ/cm$^2$.

3. Method as in claim 2, characterised in that the excimer laser is operated at a wave-length of 193 nm.

4. Method as in claim 2, characterised in that the excimer laser is operated at a wave-length of 248 nm.

5. Method as in any of claim 1 and claims 2–4, characterised in that the energy density at the workpiece is kept in the range from 400 to 1000 mJ/cm$^2$.

6. Method as in any of claim 1and claim 2–5, characterised in that the dimensions of the microstructure produced by the excimer laser range from 1 to 20000 µm.

7. Method as in any of claim 1 and claims 2–5, characterised in that the dimensions of the microstructure produced by the excimer laser range from 30 to 1000 µm.

\* \* \* \* \*